(12) United States Patent
Gono et al.

(10) Patent No.: US 8,888,680 B2
(45) Date of Patent: Nov. 18, 2014

(54) METHOD AND APPARATUS FOR FOREIGN MATTER DETECTION FOR BLOOD CONTENT SENSORS

(75) Inventors: Kazuhiro Gono, Sagamihara (JP); Takeshi Suga, Hino (JP)

(73) Assignee: Olympus Medical Systems Corp., Tokyo (JP)

(*) Notice: Subject to any disclaimer, the term of this patent is extended or adjusted under 35 U.S.C. 154(b) by 1391 days.

(21) Appl. No.: 12/168,418

(22) Filed: Jul. 7, 2008

(65) Prior Publication Data
US 2010/0004520 A1    Jan. 7, 2010

(51) Int. Cl.
| | | |
|---|---|---|
| *A61B 1/04* | (2006.01) | |
| *A61B 1/06* | (2006.01) | |
| *A61B 1/12* | (2006.01) | |
| *A61B 5/00* | (2006.01) | |
| A61B 1/00 | (2006.01) | |
| A61B 5/07 | (2006.01) | |

(52) U.S. Cl.
CPC ........... *A61B 1/041* (2013.01); *A61B 1/0638* (2013.01); *A61B 1/00009* (2013.01); *A61B 1/00057* (2013.01); *A61B 1/126* (2013.01); *A61B 5/0075* (2013.01); *A61B 5/0086* (2013.01); *A61B 5/073* (2013.01)
USPC ........... 600/103; 600/117; 600/118; 600/178; 600/476

(58) Field of Classification Search
CPC ........... A61B 1/041; A61B 1/00057; A61B 1/00009; A61B 1/0638; A61B 5/0075
USPC ............ 600/103, 157, 178, 117, 118, 476
See application file for complete search history.

(56) References Cited

U.S. PATENT DOCUMENTS

| | | | | |
|---|---|---|---|---|
| 5,406,938 A | * | 4/1995 | Mersch et al. | 600/138 |
| 5,598,842 A | * | 2/1997 | Ishihara et al. | 600/322 |
| 5,847,394 A | * | 12/1998 | Alfano et al. | 250/341.8 |
| 6,055,451 A | * | 4/2000 | Bambot et al. | 600/476 |

(Continued)

FOREIGN PATENT DOCUMENTS

| | | |
|---|---|---|
| JP | 63-145157 | 9/1988 |
| JP | 2-201251 | 8/1990 |

(Continued)

OTHER PUBLICATIONS

The International Search Report and Written Opinion by the International Searching Authority, issued on Jul. 21, 2009, in the PCT application No. PCT/JP2009/061789.

(Continued)

*Primary Examiner* — John P Leubecker

(57) ABSTRACT

Apparatus and methods for detecting foreign material obstructing a blood content sensor window to facilitate higher data accuracy from such sensors, in accordance with one embodiment of the invention for detecting foreign matter with the blood content sensor when the blood content sensor is not contacted with living tissue, an illuminator for blood content detection and the blood content sensor share a common outer window. When the window is at a distance from tissue and in absence of foreign matter on the window, all or most of the emitted light will be dispersed and little or no light will be reflected back into the sensor. Conversely, when the window is at a distance from tissue and foreign matter is present on the window, a substantial portion of the emitted light will be reflected back into the sensor indicating the presence of the foreign matter.

12 Claims, 14 Drawing Sheets

(56) References Cited

U.S. PATENT DOCUMENTS

| | | | |
|---|---|---|---|
| 6,587,711 B1* | 7/2003 | Alfano et al. | 600/476 |
| 6,772,003 B2* | 8/2004 | Kaneko et al. | 600/476 |
| 7,118,529 B2* | 10/2006 | Glukhovsky et al. | 600/160 |
| 7,479,106 B2* | 1/2009 | Banik et al. | 600/159 |
| 2004/0171915 A1 | 9/2004 | Glukhovsky | |
| 2005/0267340 A1 | 12/2005 | Ishihara et al. | |
| 2006/0069306 A1* | 3/2006 | Banik et al. | 600/118 |
| 2007/0159483 A1* | 7/2007 | Horn et al. | 345/440 |
| 2007/0206092 A1* | 9/2007 | Skala | 348/77 |
| 2007/0242140 A1* | 10/2007 | Kimura | 348/231.99 |
| 2007/0293720 A1* | 12/2007 | Bayer | 600/112 |
| 2008/0260223 A1* | 10/2008 | Davidson | 382/128 |
| 2009/0131802 A1* | 5/2009 | Fulghum et al. | 600/478 |
| 2010/0329520 A2* | 12/2010 | Gono et al. | 382/128 |
| 2011/0060189 A1* | 3/2011 | Belson | 600/117 |

FOREIGN PATENT DOCUMENTS

| | | |
|---|---|---|
| JP | 5-103746 | 4/1993 |
| JP | 11-221190 | 8/1999 |
| JP | 2005-328990 | 12/2005 |
| WO | 02/073507 | 9/2002 |
| WO | WO 2006005075 A2 * | 1/2006 |

OTHER PUBLICATIONS

The extended European Search Report by the European Patent Office, issued on May 29, 2012, in the related European Patent Application No. 09794337.7.

The English translation of the Japanese Office Action, issued on Jun. 11, 2013, in the corresponding Japanese application No. 2010-546569.

* cited by examiner

METHOD AND APPARATUS FOR FOREIGN MATTER DETECTION FOR BLOOD CONTENT SENSORS

FIELD OF THE INVENTION

The present invention relates generally to the utilization of light scattering and absorption techniques to detect possible obstructions or foreign matter on blood content sensor lenses. More specifically, the invention relates to an apparatus and method for utilizing light to detect foreign matter on the window sensor of a blood content sensor system.

BACKGROUND OF THE INVENTION

Scientists have discovered that a detectible increase in the blood content of superficial mucous membrane occurs proximate cancerous and precancerous lesions in the colon relative to the blood content of healthy tissue as described in, for example, R K Wali, H K Roy, Y L Kim, Y Liu, J L Koetsier, D P Kunte, M J Goldberg, V Turzhitsky and V Backman, Increased Microvascular Blood Content is an Early Event in Colon Carcinogenesis, Gut Vol. 54, pp 654-660 (2005), which is incorporated by reference herein. This phenomenon is referred to as early increase in blood supply (EIBS).

Relying on this phenomenon, it is known that it is possible to predict an area of potential abnormality based on early increase in blood supply (EIBS) in the area of abnormality. Further, it has been discovered, that by using a probe applying collimated light to an area of interest, and detecting the amount of absorbed and reflected light it is possible to provide blood content or blood flow information to a clinician to guide an endoscope to detect a possible abnormality in vivo without an invasive procedure. Such techniques have been described for example in U.S. patent application Ser. No. 11/937,133 filed on Nov. 8, 2007, issued as U.S. Pat. No. 8,162,828 entitled "Blood Content Detecting Capsule", assigned to the assignee of the present invention, which is incorporated by reference herein.

Typically, blood content or blood flow detection relies on measuring the amount of light reflected from the tissue mucosa back into the blood content sensor. Because systems rely on measuring the amount of reflected light, the accuracy of the measurements are greatly impacted if the blood detection apparatuses window is obstructed by foreign liquid or solid matter on the lens. Further, the accuracies of any measurement or foreign matter detection techniques are impacted if there is extraneous light detected by the sensors as a result of other observation devices such as a traditional CCD camera light.

Various techniques exist for removing foreign liquid or solid matter from endoscope lenses while in vivo, e.g., nozzle sprayers of water onto the endoscope or blood content sensor windows, however, techniques still lack a method to detect if the observation window is actually clean. In an observation only system, i.e., one without a blood content sensor, an operator may determine if there is foreign matter on the observation window by subjectively viewing of the image. However, in blood content sensor systems, there is no viable image for an operator to view, therefore an operator cannot make a determination about the presence of foreign matter on the detector window.

Further, when it is desirous to determine the presence of foreign matter on the blood content sensor window, the endoscope tip or blood content sensor window is removed from the surface of the tissue. As a result, illumination light from the scope observation source, e.g., endoscope camera, may be scattered by the surface of the living tissue and reach the receiving fibers of the blood content sensor. In that case, a false reading of the level of foreign matter present will occur because light from the observation source is attributed to the blood content sensor itself, thereby falsely determining the presence or absence of foreign matter.

Accordingly, in order to improve the accuracy of blood content measurements there needs to exist a technique for objectively determining if the measurement lens is obstructed by foreign matter.

SUMMARY OF THE INVENTION

Systems and methods that detect liquid and solid foreign matter on the blood content sensor of the present invention advantageously facilitate higher data accuracy from such sensors. Further aspects of the invention minimize the amount of extraneous light that enters the blood content sensor during periods of foreign matter detection. In one exemplary embodiment using blood content sensors with a scope, such as an endoscope or colonoscope, independent light sources are alternatively activated to sequentially produce light for (1) blood content detection and foreign matter detection and (2) observation through the scope by a clinician. In particular, light for scope observation is emitted at time intervals between the time intervals that separate light is emitted for use in blood content detection or foreign matter detection. In this manner, potential adverse effects are reduced for any extraneous light generated for scope observation will be reflected into the blood content detection window during blood content or foreign matter detection.

In accordance with another embodiment of the invention, light of different wavelengths or ranges is used for the respective functions of scope observation and blood content detection (including foreign matter detection). The detection of foreign matter on the blood content sensor, and accordingly the detection of blood content abnormalities are improved as a result of the different light wavelengths used for scope observation and that used for blood content detection.

DETAILED DESCRIPTION

Figure 1:
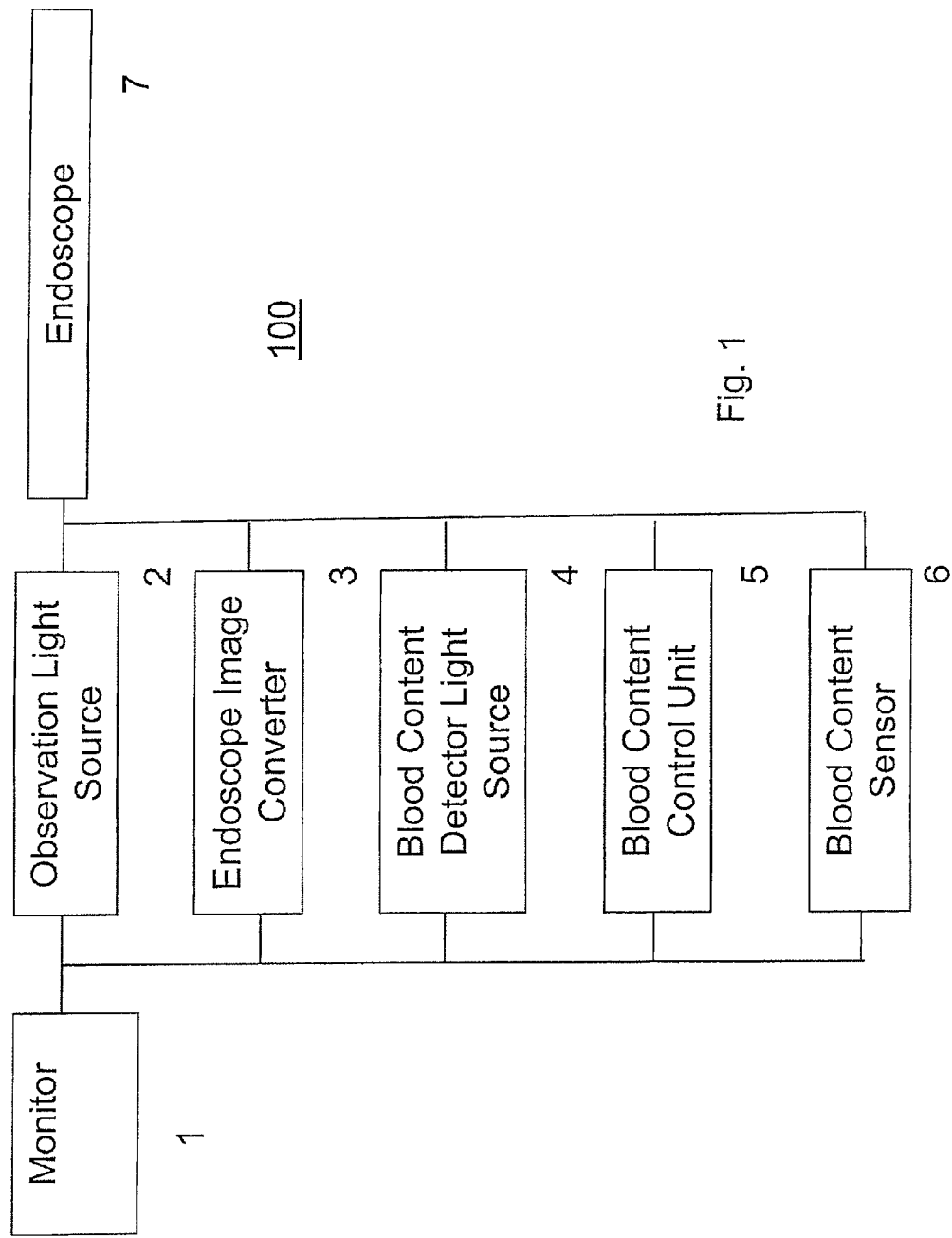
FIG. 1 illustrates a block diagram of an exemplary system in accordance with one aspect of the invention utilizing blood content sensors.

The present invention relates generally to improvements in detection of deleterious foreign liquid or solid matter that may deposit on blood content sensors. Such improvements are advantageously usable with blood content sensors implemented with, for example, traditional and capsule-type endoscope configurations.

Particular blood content sensors for detecting blood content or blood flow such as for example, those described in the above referenced previously filed U.S. patent application Ser. No. 11/937,133, issued as U.S. Pat. No. 8,162,828 typically operate when in direct contact with living tissue, such as mucosa tissue. As used herein, blood content sensors refer to sensors refer to sensors that detect blood content or blood flow. One principle of the invention is based on foreign matter detection with the blood content sensor when the blood content sensor is not contacted with living tissue. In such instance, an illuminator for blood content detection and the blood content sensor share a common outer window. When the window is at a distance from tissue and in absence of foreign matter on the window, all or most of the emitted light will be dispersed and little or no light will be reflected back into the sensor.

If, however, foreign matter is present on the window, then an easily measurable quantity of emitted light will be reflected back through the common window by the foreign matter. Accordingly, if, for example, the intensity of reflected light is equivalent to or higher than a predetermined threshold when such window is not in contact with tissue, then it can be presumed that foreign matter is present on the window. It is understood by those skilled in the art that many configurations are conceivable that exploit this elementary concept in detecting the presence of foreign matter on a sensor.

Referring to the drawings, like numbers indicate like parts throughout the views as used in the description herein, the meaning of "a," "an," and "the" includes plural reference unless the context clearly dictates otherwise. Also, as used in the description herein, the meaning of "in" includes both "in", and "on" unless the context clearly dictates otherwise. Also, as used in the description herein, the meanings of "and" and "or" include both the conjunctive and disjunctive and may be used interchangeably unless the context clearly dictates otherwise.

FIG. 1 depicts a block diagram of an exemplary endoscope system 100 containing a blood content detection sensor 6. System 100 further contains video monitor 1, observation light 2, endoscope image converter 3, blood content sensor light 4, blood content control unit 5 and endoscope 7.

A conventional endoscope configuration is usable for endoscope 7 in accordance with the invention. Consequently, in typical observation mode, endoscope 7 is inserted proximate living tissue such as, for example, the colon or other tissue along the gastrointestinal track. Observation light source 2 generates light that is transmitted via endoscope 7 and reaches the surface of the target living tissue. Light is reflected off the tissue under investigation and reenters endoscope 7 through a series of lenses. The reflected image is processed by endoscope image converter 3 which may contain a CCD or other image processing device creating digital signals representing an image of the target tissue. The signals from image converter 3 are transmitted to monitor 1 where they are converted into a video image displayed to an operator or clinician.

However, unlike conventional endoscopes that system 100 is also operable in a blood content measurement mode. In blood content measurement mode, blood content light source 4 generates light to be conveyed to endoscope 7. Endoscope 7, while contacting the tissue mucosa under investigation, illuminates the tissue with the light from blood content sensor light source 4 and then receives back at the blood content sensor 6, scattered or reflected, i.e., interacted light, from the underlying tissue. The interacted light is conveyed by the sensor 6 to the blood content control unit 5, such as by an optical or electrical signal.

The blood content control unit 5 receives this data and provides it to a data preprocessor, that executes, for example, a data correction algorithm, such as white correction represented in the following equation (1).

$$\Delta Ic(\lambda) = \frac{\Delta I(\lambda)}{\Delta Iw(\lambda)} = \frac{I_\Pi(\lambda) - I_\perp(\lambda)}{Iw_\Pi(\lambda) + Iw_\perp(\lambda)} \tag{1}$$

Where the symbols $\pi$ and $\perp$ used in the numerator and denominator of equation (1) represent the spectrum of horizontally polarized light and the spectrum of vertically polarized light, respectively. In equation (1), $\lambda$ represents wavelength, $\Delta I(\lambda)$ indicates the measured difference polarization spectrum, $\Delta Iw(\lambda)$ is the spectrum measured using a standard white plate and is calculated by summing the white horizontal polarization spectrum $Iw\pi(\pi)$ and the white perpendicular polarization spectrum $Iw \perp(\lambda)$, as shown in the denominator of equation (1). In the numerator of equation (1), the difference between the horizontal polarization spectrum $I\pi(\lambda)$ and the perpendicular polarization spectrum $I \perp(\lambda)$ is calculated and a signal indicative of $\Delta I(\lambda)$.

The blood content control unit 5 calculates the blood content by using equation (2) below, which is shown in, for example, M. P. Siegel et al. "Assessment of blood supply in superficial tissue by polarization-gated elastic light-scattering spectroscopy," Applied Optics, Vol. 45, Issue 2, pp. 335-342 (2006).

$$\Delta I(\lambda) = \Delta I_{scattering}(\lambda) \exp[-\alpha A_{PG}(\lambda)] \tag{2}$$

Blood content control unit 5, using a model equation, such as equation (2), provides a corresponding blood content value to monitor 1 or other display devices. Alternatively, the blood content control unit 5 may also provide the blood content value to a data validator as a check on the integrity of the collected data. Blood content control unit 5 may also provide the results from the sensor 6 to a comparator unit (not shown) to determine the validity of a measurement and to improve the accuracy of detection based on the measurement window.

In foreign matter detection mode operation in accordance with one aspect of the invention, the endoscope 7 is positioned with the sensor 6 a distance from the tissue under investigation. In such operation mode, light is generated by blood content sensor light 4 and reflected light is detected, by sensor 6 and correspondingly measured and processed by blood content unit 5. If no foreign matter is present on the external sensor window then all or most of the light will be emitted through the window and will be dispersed. Very little light will be reflected and subsequently detected by sensor 6. If however, foreign matter has deposited on the detection window, then a detectable amount of light will be reflected back by the foreign matter and into the sensor 6. Accordingly, if the intensity of the reflected light that is detected is equivalent to or higher that a predetermined threshold then it is presumed that foreign matter has deposited on the window and that the reflected light that is detected is a result of reflection off of such foreign matter.

Figure 2:
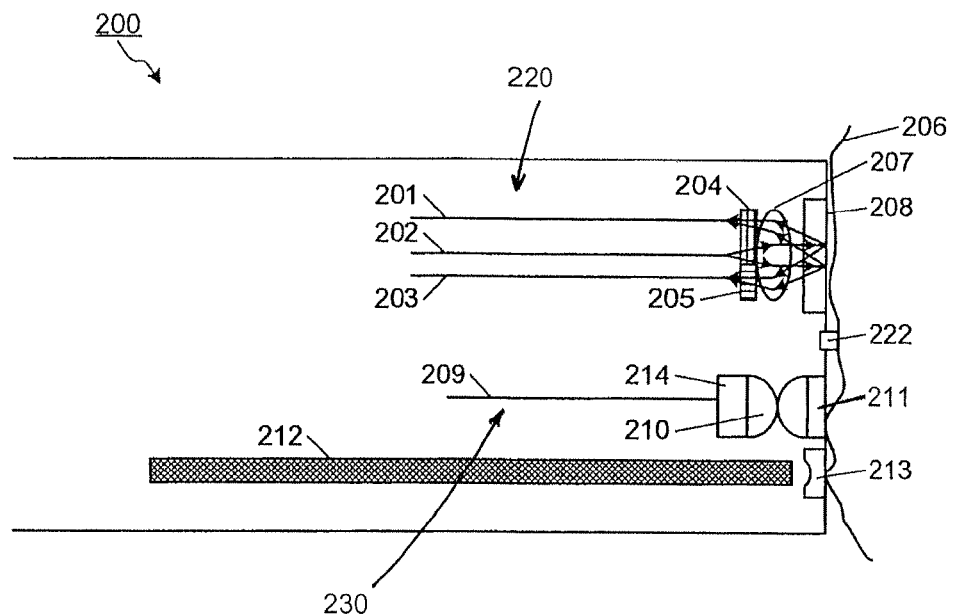
FIG. 2 illustrates a cross sectional view of an exemplary embodiment of an endoscope tip containing a blood content sensor in contact with tissue mucosa.

More detailed operation of such exemplary system will now be described with respects to FIGS. 2 and 3. Referring to FIG. 2, the tip of endoscope system 200 comprising a blood content detection section 220 and an optical observation section 230. The blood content or section 220 contains receiving fibers 201 and 203, illumination fiber 202, linear polarizers 204 and 205, lens 207, blood content detection window 208. Observation section 230 contains light transmission fiber 212, illumination window 213, observation window 211, observation lens 210, imaging unit 214, such as a CCD or other imaging device, and transmission line 209. The receiving fibers 201 and 203 may be coupled to the blood content sensor control unit 5 of FIG. 1.

FIG. 2 further depicts the system 200 in a blood content detection position, i.e., in contact with tissue 206. During operation, light from the blood content sensor source is conveyed on illumination fiber 202 through polarizer 204. The emitted polarized or collimated light passes through lens 207 and enters blood content detection window 208. The emitted light strikes tissue 206 and is scattered and reflected based on the interaction with the tissue 206. The reflected light passes back through blood content window 208 and through lens 207. Light passing through polarizer 204 is aligned with the transmitted light since it passes through the same polarizer 204. In the depicted embodiment, polarizer 205 is orthogonal to polarizer 204 and any light passing through it is accordingly conveyed to receiving fiber 203 represents collimated light with a different angle of polarization relative to the transmitted light.

Because the tip of the endoscope 200 is in contact with the tissue mucosa 206 during blood content detection measurement, the image received via observation lens 210 and conveyed to imaging unit 214 is obstructed and may be washed out. Because all the light emitted by 213 is absorbed by tissue 206, there is no area of tissue illuminated for the operator to observe.

Prior to performing any blood content detection, the operator will have to make a determination regarding whether the blood content sensor window 208 is sufficiently clean of obstructions or foreign matter to determine whether a blood content measurement should be performed or whether the lens and window should be rinsed to remove the foreign matter by any one of known techniques, including for example use of spray nozzle on the endoscope tip or a water flow outlet in the endoscope tip. These determinations may be made when the blood content sensor 220 is not in contact with the underlying tissue 206.

In order to determine if the blood content sensor 220 in the tip of the instrument 200 is in contact with the tissue, it is possible to use, for example, either a mechanical or electromagnetic contact sensor such as sensors 222, or by observation by an operator through lens 210 and 211. When the blood content sensor 220 is not in contact with tissue 206, it is possible to perform a foreign matter measurement. Suitable contact sensors like sensor 222 to indicate contact with the tissue mucosa may include, for example, specifically designed endoscopes, pressure sensors, balloons, or the like. Such contact sensors are likewise suitable for blood content sensors employed in instruments other than endoscopes or employed alone.

Figure 3:
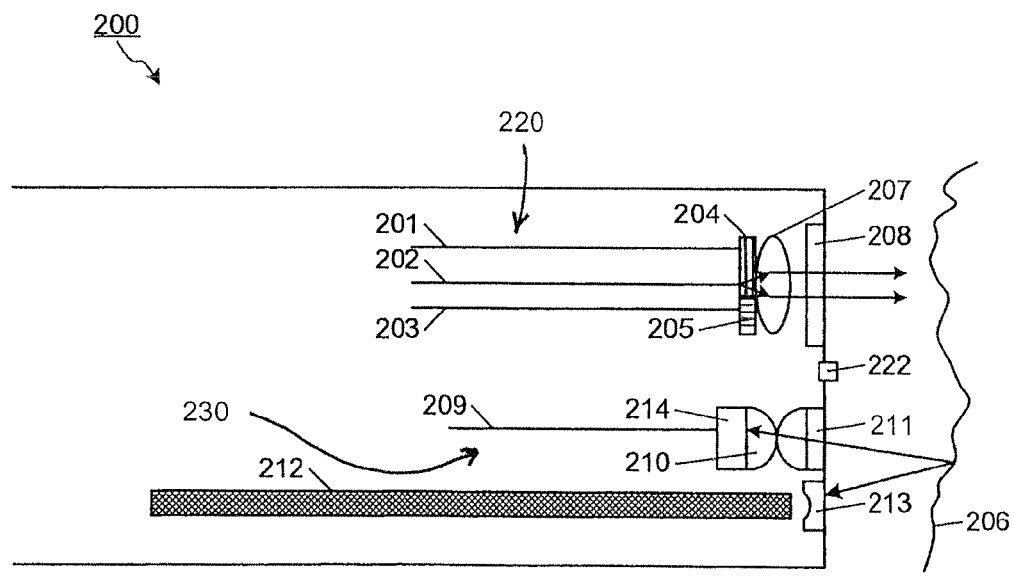
FIG. 3 illustrates the exemplary embodiment of the endoscope tip in FIG. 2 not in contact with the tissue mucosa.

In FIG. 3, the tip of system 200 is depicted at a distance from and not in contact with the tissue mucosa 206. Accordingly, in this position, illumination window 213 and blood content detection window 208 are not in contact with tissue 206 and not in a position to perform a blood content measurement. During operation in this position, observation light is transmitted on light transmission fiber 212 to illumination window 213. Light emitted from window 213 strikes tissue 206 and illuminates an area to be observed. The reflected light enters observation window 211 and is focused through lens 210 onto imaging unit 214. The image signals generated from imaging unit 214 are conveyed on transmission line 209 to a display, such as monitor 1 of FIG. 1 for observation by a clinician.

Also, in the tip position shown in FIG. 3, the light exiting illumination window 213 may be reflected back through blood content detection window 208 and be received on receiving fibers 201 and 203 and then processed by the blood content sensor control unit 5 of FIG. 1. If this occurs during a period of time when the blood content sensor is determining the presence or absence of foreign matter on window 208, a false reading may occur regarding the existence of foreign matter on the blood content detection window 208. Such a result may yield an incorrect reading. To eliminate this undesirable occurrence, the timing of the activation of the observation light transmitted on illumination transmission fiber 212 and light transmitted on blood content illumination fiber 202 are such that light is not simultaneously emitted by the fibers 212 and 202.

Figure 5:
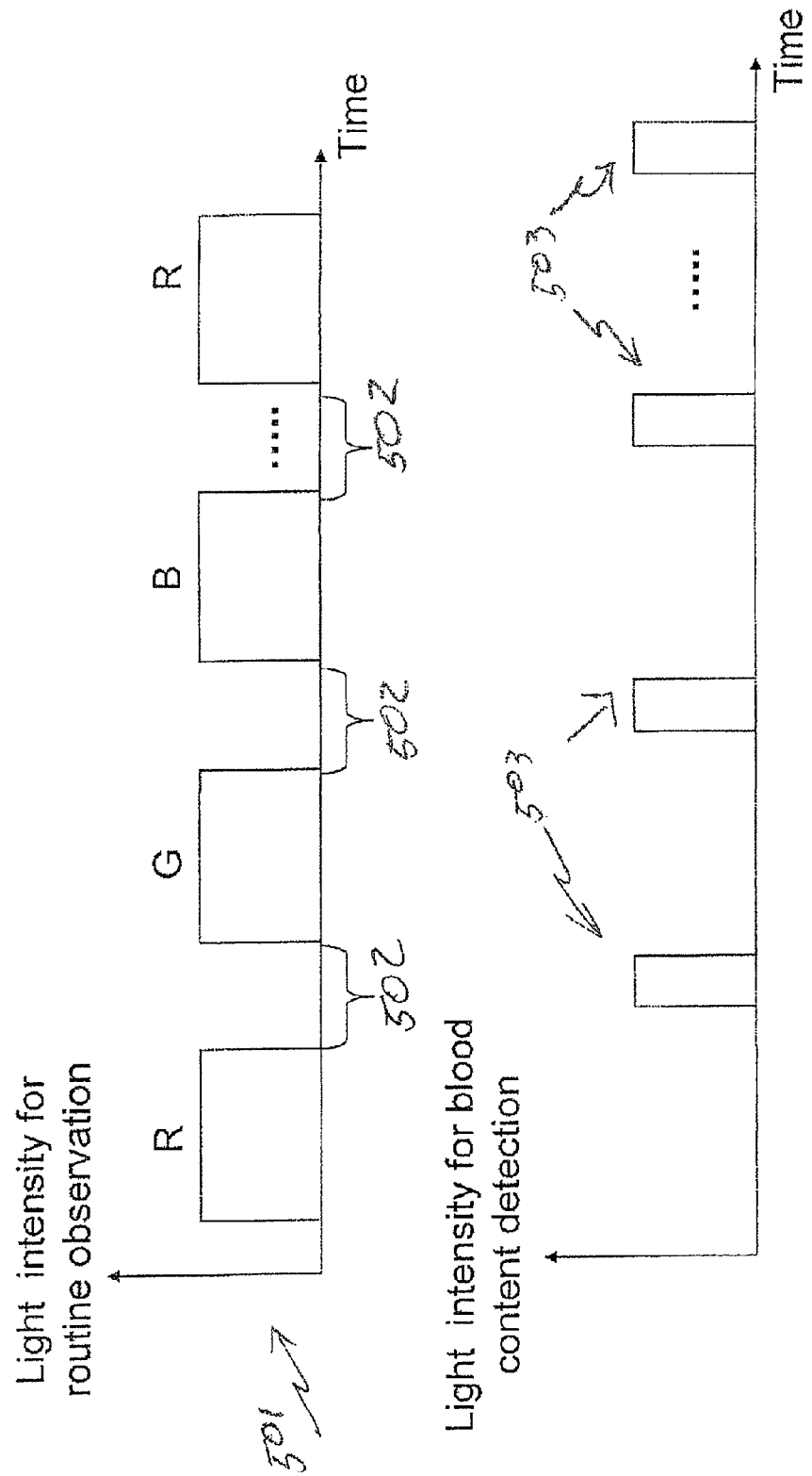
FIG. 5 illustrates an exemplary diagram of light intensity vs. time of the observation and detection lights in accordance with an aspect of the invention.

FIG. 5 illustrates an exemplary timing sequence for use with an embodiment of the present invention. As seen in timeline 501, illumination for scope observation by a clinician is generated by a first light source and emitted from observation window 213 in the sequence order oft for example, red light, green light, and then blue light during the intervals R, G and B, respectively. At such time intervals as shown in FIG. 3, the light is reflected off the tissue 206 and enters lens 210 and is focused on imaging unit 214. Imaging unit 214 may, for example, be a monochrome CCD or color CCD or other image capturing device. The corresponding digital or analog image signals produced by the imaging unit 214 are then transmitted on transmission line 209 for display to the operator.

At time intervals, during the off or shielded periods 502 in FIG. 5 between the red, green, and blue illumination sequence intervals R, G and B, used for observation, blood content detection light 503 is transmitted on fiber 202 for emission out of blood content detection window 208 to detect foreign matter. Because the blood content sensor 220 in FIG. 3 is not in contact with the underlying tissue, only a minimum amount of transmitted light should be reflected into the blood content detection window 208 if no foreign matter is present on said window 208. Further, because the blood content sensor light is transmitted during the periods 502 in FIG. 5 when the observation light is off or shielded, the possibility of extraneous light used for observation entering the blood content window 208 and interfering with this reading is eliminated.

Accordingly, during intervals 502, if the intensity of the light used for blood content detection is measured and found to be equivalent to or higher than a threshold level such as, for example, approximately 10% of the intensity typically detected for interacted light when the blood content sensor 220 is in contact with the tissue 206 then it is presumed that the blood content sensor light is being reflected by foreign matter disposed on the window 208. Once it is known that foreign matter is present, an operator may take the appropriate steps to remove such matter.

Figure 6:
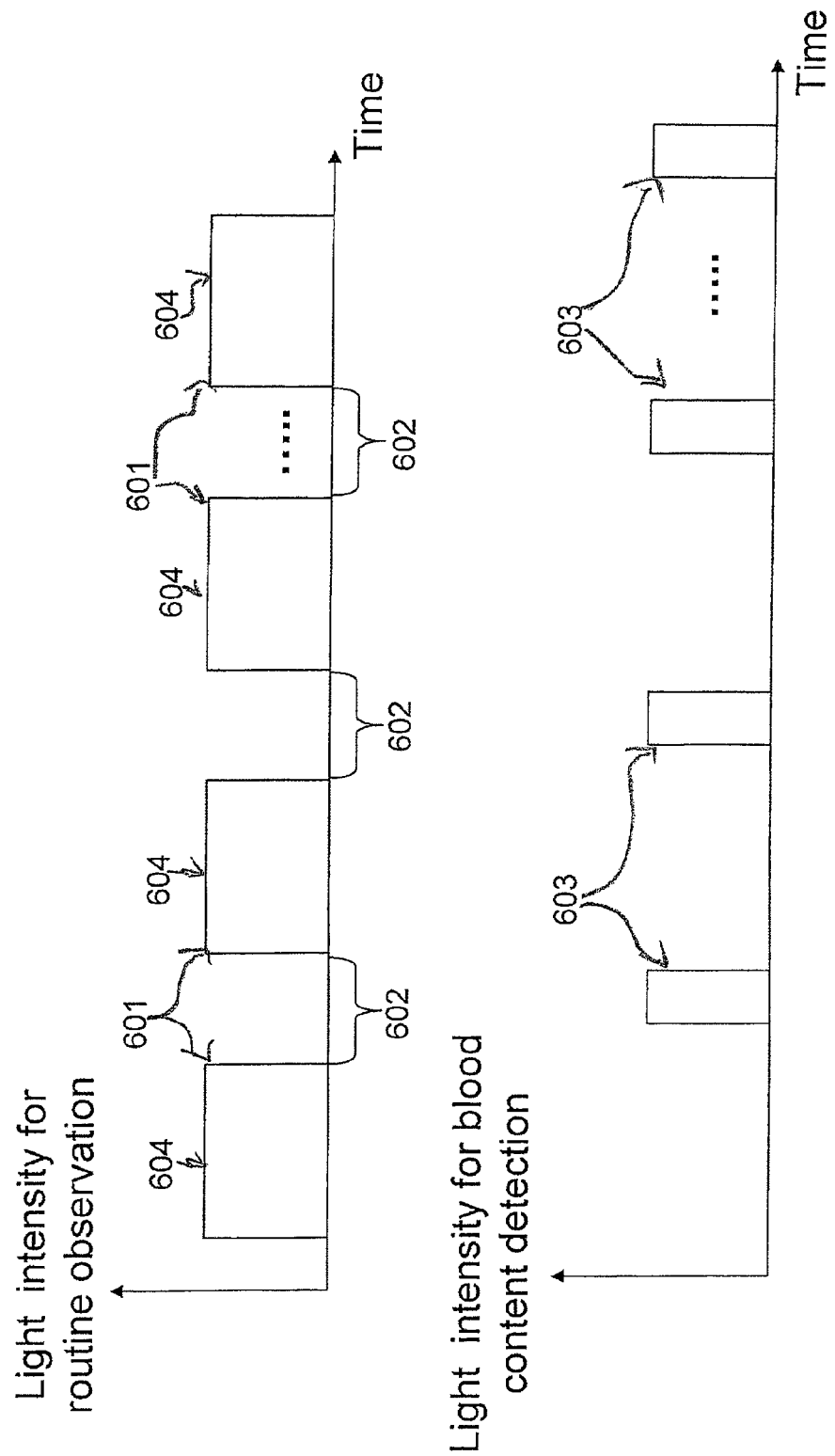
FIG. 6 illustrates an exemplary diagram of light intensity vs. time of the observation and detection lights in accordance with another aspect of the invention.

FIG. 6 illustrates an alternative timing sequence useable in accordance with another embodiment of the present invention. Rather than sequentially transmitting red, green, and blue light for scope observation as shown in FIG. 5, broad band light 601 in, for example, the 400 to 700 nm wavelength range may be alternatively transmitted during intervals 604 and then shielded during intervals 602. During the shielding intervals 602, the light used for blood content detection 603 is generated to detect foreign matter or to perform blood content measurements. In accordance with this embodiment, the wavelength of light used for illumination 601 and measurement 603, including the detection of foreign matter from the blood content sensor is not particularly limited. For example, light in the 500 to 600 nm wavelength range may also be used as described in M. P. Siegel, et al., Applied Optics Vol. 45, No. 2 pp. 335-342, 2006, which is incorporated by reference herein.

In another embodiment of the present invention, generated light used for scope observation by a clinician is at different wavelengths than light used for blood content detection and foreign matter detection. As a consequence, in this embodiment light generated for scope observation and for the blood content sensors as separated in frequency (or wave-length) as opposed to time as shown in FIGS. 5 and 6. In this exemplary wavelength-based embodiment, the endoscope 7 of FIG. 1 emits broad-band illumination light in, for example, the wavelength range of the 400 to 700 nm in a continuous manner rather than as sequentially pulses. Because of the use of broad-band light in the 400 to 700 nm wavelength range, a color CCD may be used for acquiring images for scope observation. Such an arrangement is illustrated in FIG. 7.

Figure 7:
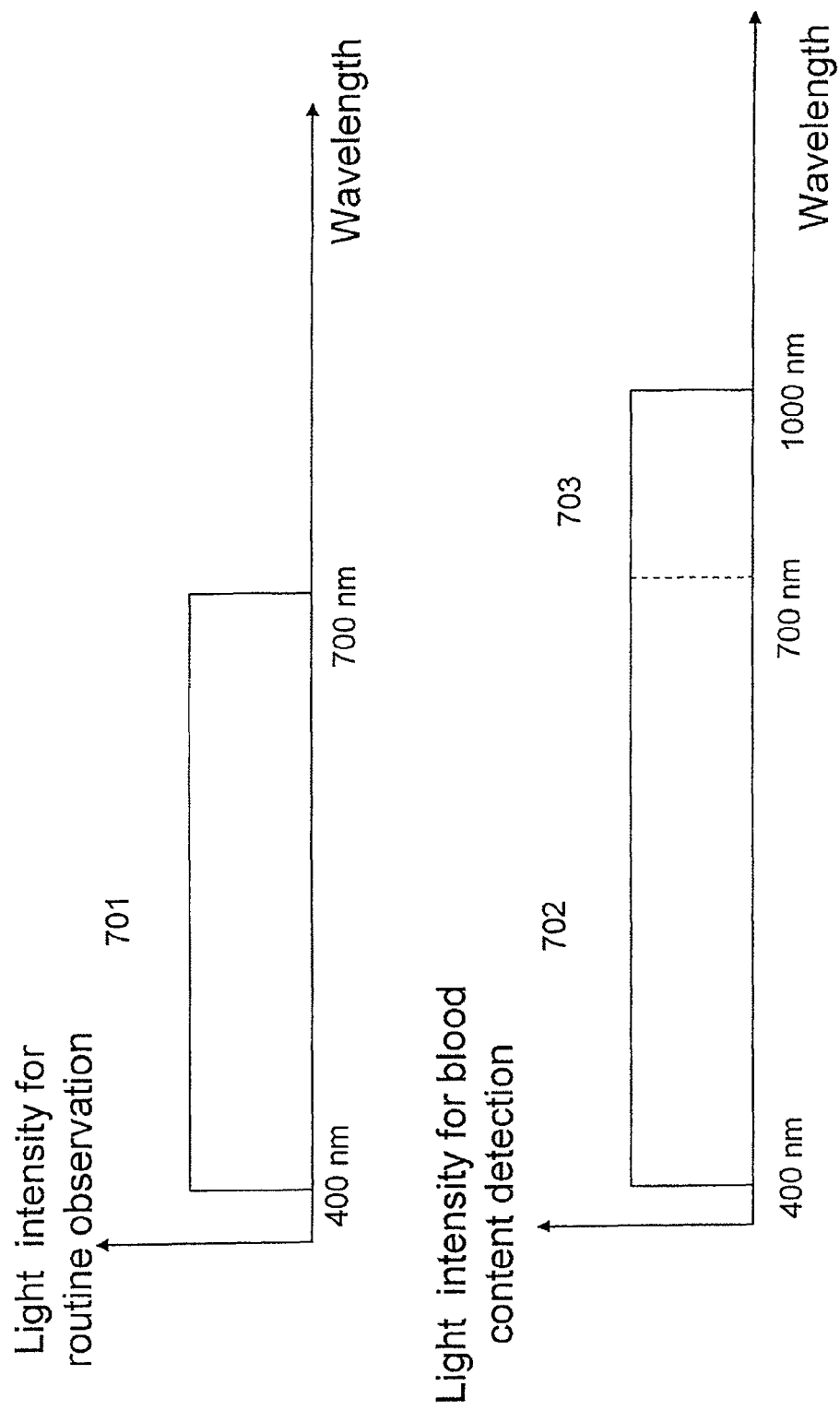
FIG. 7 illustrates an exemplary diagram of light intensity vs. wavelength of the observation and detection lights in accordance with further aspect of the invention.

As seen in FIG. 7, light 701 in the 400 to 700 nm range is used for scope observation. Light 702, also in the 400 to 700 nm range is further used for blood content detection and light 703, a different range such as, for example, in the 700 to 1000 nm range would only be used for foreign matter detection. This embodiment will now be described in conjunction with FIGS. 2 and 3. Light 701 may be continuously emitted or pulsed from observation window 213. During the periods when the probe is not in contact with tissue 206, reflected light will enter observation window 211 and be conveyed to color imaging unit 214. The image will then be conveyed on transmission line 209 for observation on an external monitor. Simultaneously, the blood content sensor will be emitting light 702 and 703 from transmission fiber 202. Light 702 and 703 will strike tissue 206 and, if there is no foreign matter present, only minimal amounts of light will be reflected back into receiving fibers 204 and 205.

Because light 703 is of a different wavelength range than light 701 or 702, any extraneous light 701 or 702 that might be received back by receiving fibers 204 and 205 will not impact the foreign matter detection measurement. If detected light intensity in the 700 to 1000 nm range exceeds a threshold value, such as, for example, approximately 10% of the intensity typically detected for interacted light when the blood content sensor 220 is in contact with the tissue 206, during the time when the probe is not in contact with tissue 206, then the operator clinician may presume that foreign matter is present, and can take the necessary cleaning steps to remove it.

During the period when the probe is in contact with tissue 206, any light generated for scope observation, 201 in the 400 to 700 nm wavelength and conveyed though observation window 213 will not enter blood content sensor window 208 and receiving fibers 201 and 203 because of the contact with the underlying tissue. In this manner no false blood content readings will occur. In contrast, when the probe is not in contact with tissue 206, the extra light transmitted from transmission fiber 202 will aid in illumination for general observation.

Figure 8:
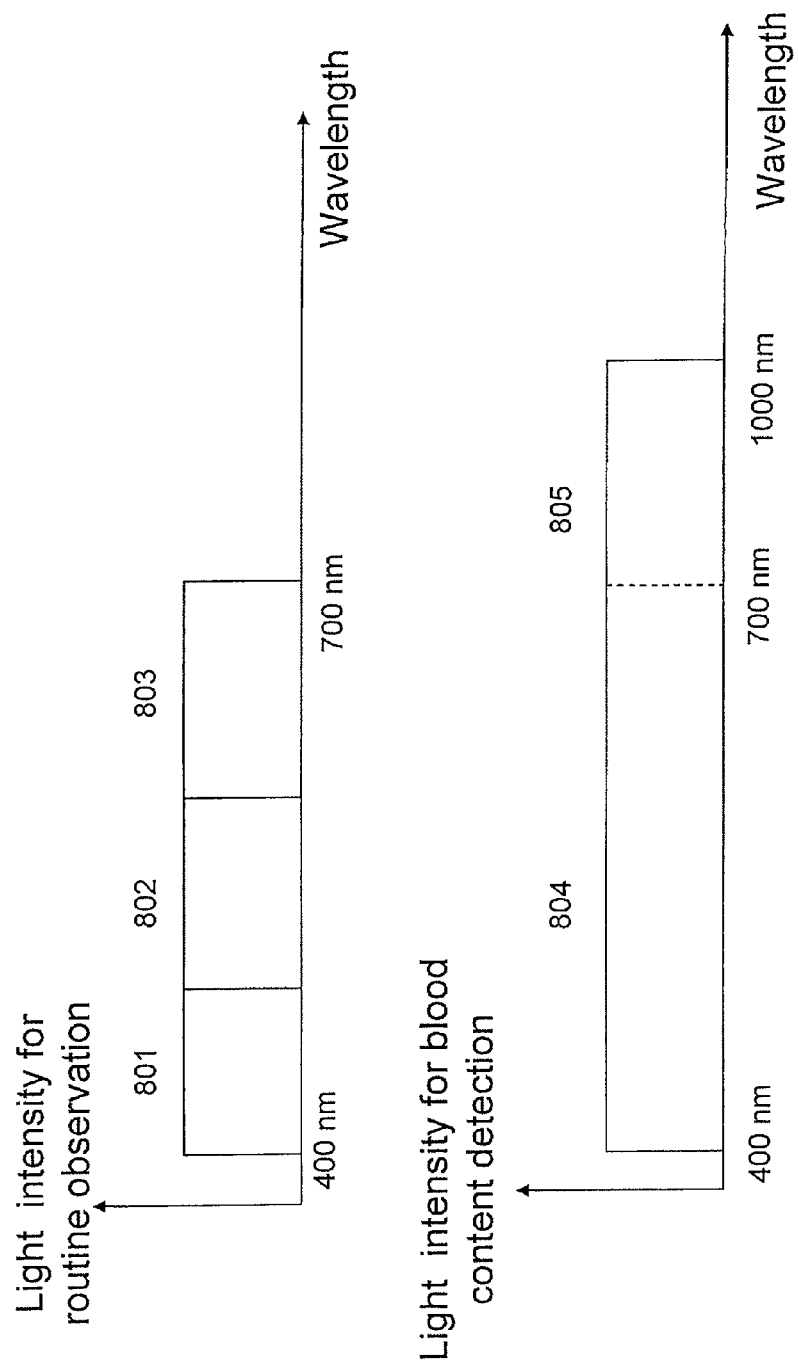
FIG. 8 illustrates an exemplary diagram of light intensity vs. wavelength of the observation and detection lights in accordance with yet another aspect of the invention.

In an alternative exemplary embodiment depicted by FIG. 8, light 801-803 for scope observation is sequentially emitted in the order of red light 801, green light 802 and blue light 803 and covers light in the 400 to 700 nm range. Light used for blood content detection 804 may also be in the 400 to 700 nm range while light 805 used for foreign matter detection is emitted in the 700 to 1000 nm range. Such an exemplary configuration may be applied in a frame-sequential system that sequentially emits the red light 801, green light 802, and blue light 803 rather than a continuous system that utilizes continuous broad-band light.

Because of the separation of light by wavelength, between the light used for foreign matter detection 805 and the light used for scope observation 801 to 803, there is no interference when the blood content sensor is performing a foreign matter detection measurement. Accordingly, if the light received by fibers 201 and 203 in the 700 to 1000 nm range exceeds a threshold, then the operator may presume that foreign matter is disposed on the window of the blood content sensor.

Figure 9:
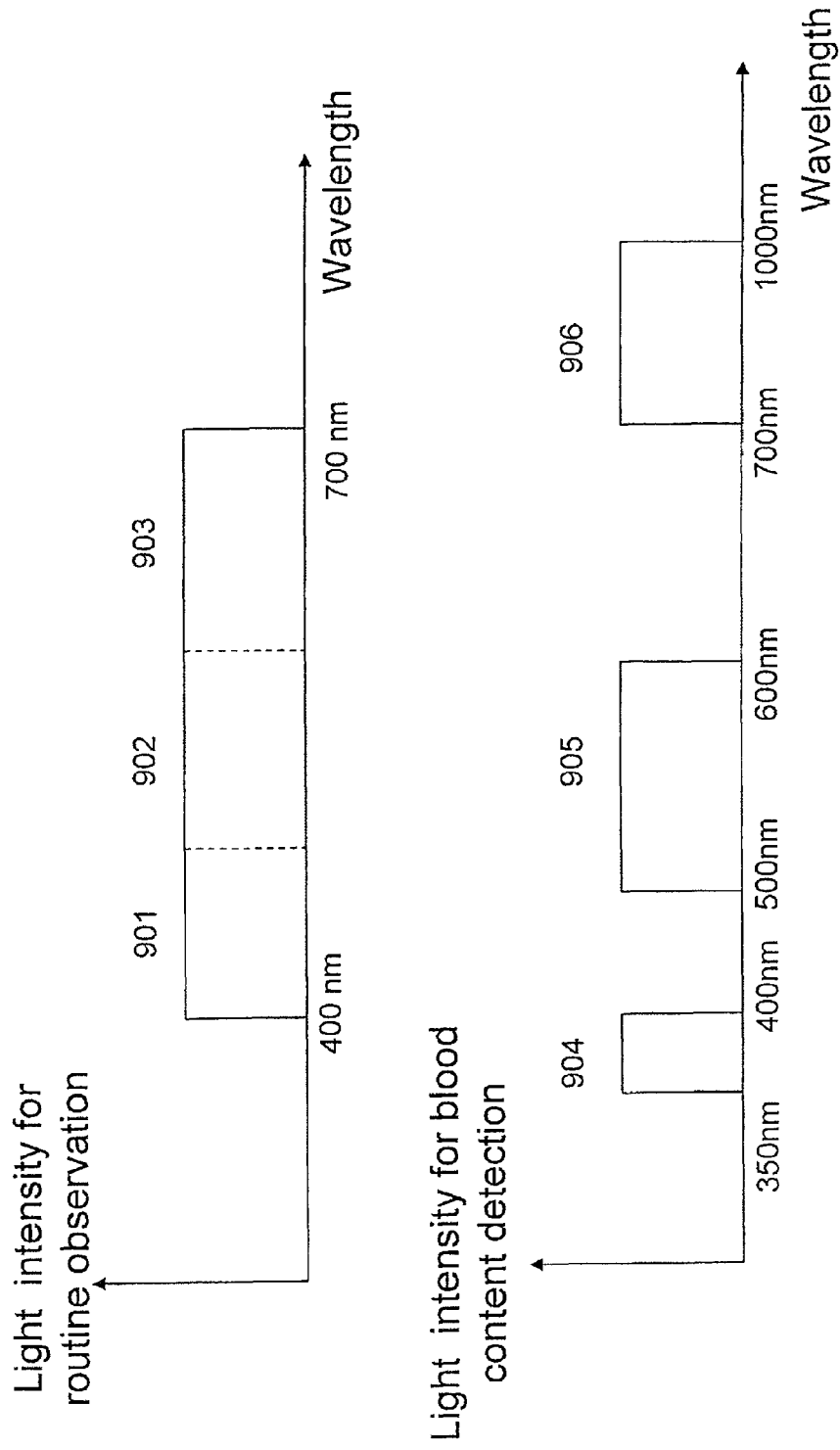
FIG. 9 illustrates an exemplary diagram of light intensity vs. wavelength of the observation and detection lights in accordance with another aspect of the invention.

FIG. 9 depicts an alternative embodiment light configuration of the present invention. In this embodiment, light used for blood content measurement and scope observation is not particularly limited. Advantageously, light for scope observation may be continuous covering the wavelength spectrum of, for example, 400 to 700 nm or may be sequentially transmitted as red light 901, green light 902 and blue light 903. Light for blood content detection 905 may be in the 500 to 600 nm wavelength range, and light for foreign matter detection 904 and 906 may be in the 350 to 400 nm or 700 to 1000 nm wavelength range respectively.

Figure 10:
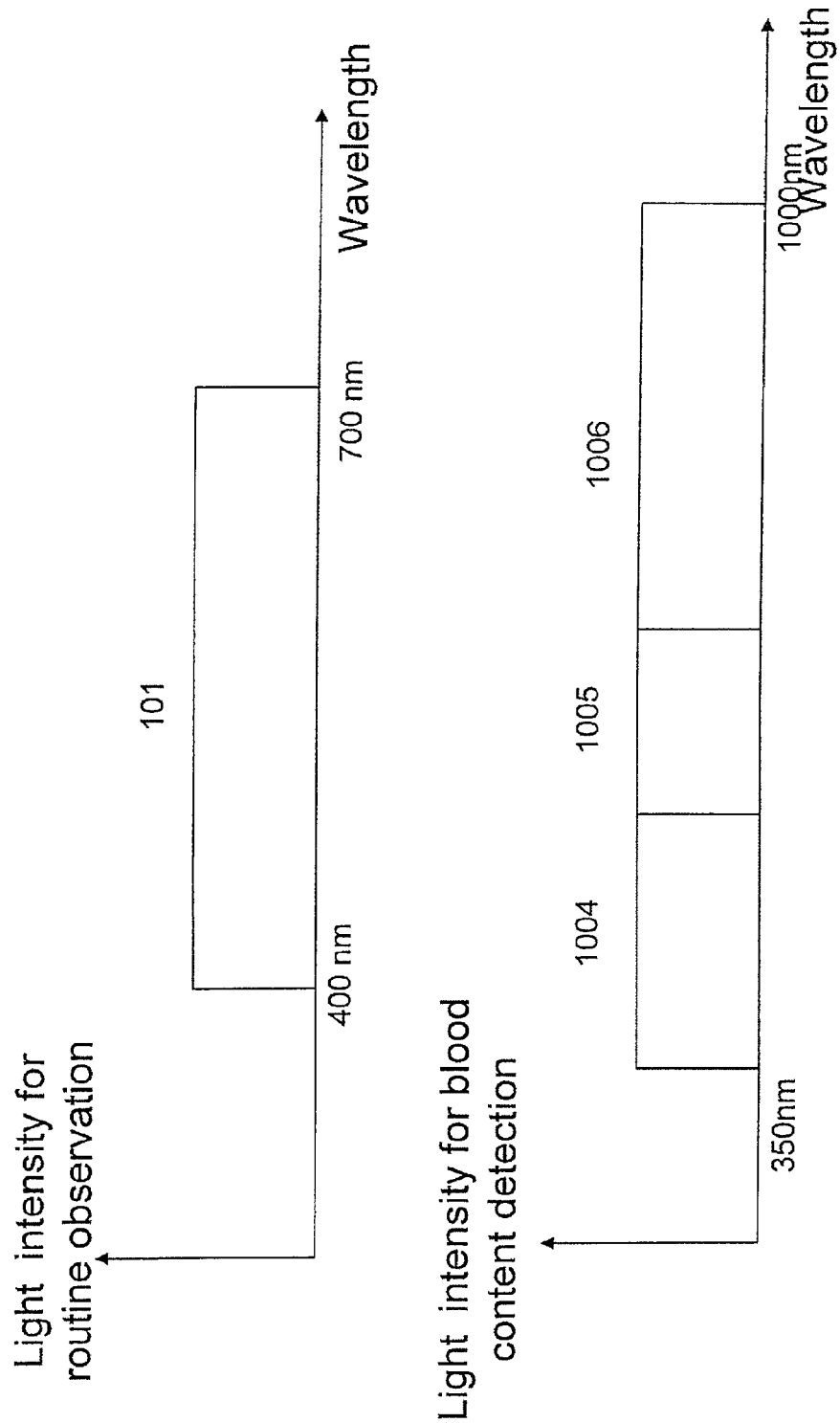
FIG. 10 illustrates an exemplary diagram of light intensity vs. wavelength of the observation and detection lights in accordance with a further aspect of the invention.

In another embodiment described with reference to FIG. 10, foreign matter detection is advantageously accomplished by utilizing a total spectrum for observation broader then that spectrum used for calculating blood content detection alone. Such an embodiment yields a higher isolation of illumination light for scope observation, thereby improving the accuracy of the foreign matter detection. When detecting foreign matter, generally the larger the range of wavelengths covered by the blood content sensor, the higher the signal-to-noise ratio will be, yielding an improvement in foreign matter detection. Because light emitted from observation window 208 is scattered near the surface of tissue 206, the measurable energy of light received at receiving fibers 201 and 203 is likely to be low.

Accordingly, it is advantageous to provide a system that has sufficient sensitivity for detecting very weak signals reflected by foreign matter on the blood content measurement window 208. By detecting foreign matter with a broad wavelength of light, overall sensitivity is improved. As seen in FIG. 10, scope observation light 101 is sequentially emitted in the 400 to 700 nm wavelength range to form a continuous signal. Light 105 is utilized for blood content detection and falls within the range of 350 to 1000 nm wavelength, and preferably, in the 500 to 600 nm range. Light wavelength range 104 and 106 surround light wavelength range 105 and encompass a range broader than the light range 101, for example, making up the range from 350 to 1000 nm wavelength. In this manner foreign matter detection requires that light 104 and 106 be detected at a sufficient level to indicate foreign matter on window 208. Because of the broader spectrum of light to detect. The corresponding light energy received by the blood content sensor may advantageously be higher than for a narrower band of light.

Figure 11:
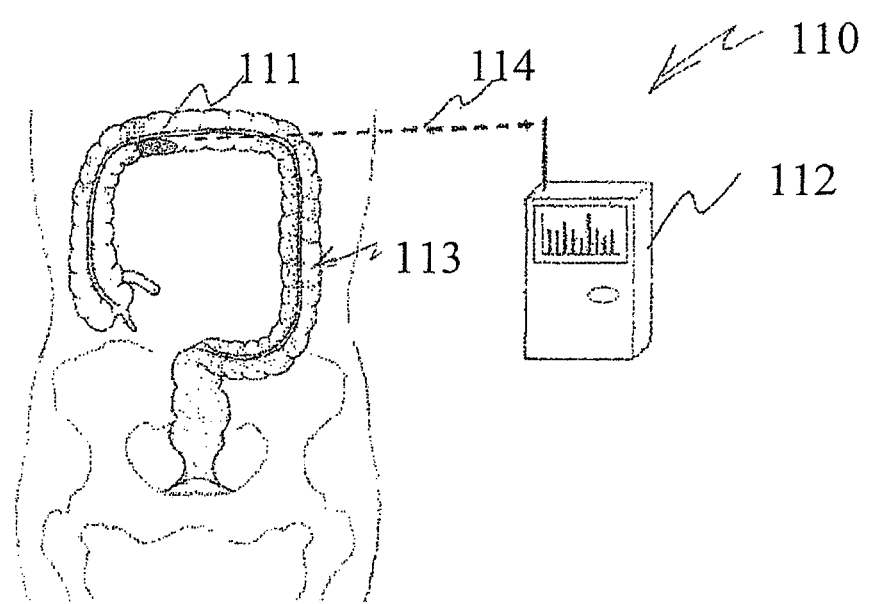
FIG. 11 depicts an exemplary capsule endoscope system in incorporating aspects of the present invention.

In addition to traditional endoscope techniques, the foreign matter detection techniques of the present invention are equally applicable to capsule type endoscopes as well. FIG. 11 shows an exemplary embodiment of a capsule type endoscope system in use within a patient.

System 110 includes a capsule endoscope 111 and a host processing unit 112. Capsule endoscope 111 is inserted into an organ such as a colon 1131 or ingested orally by a patient. Capsule endoscope 111 wirelessly transmits, represented by reference 114, to host processing unit 112. The wireless transmission can be any known transmission method including known wireless methods such as induction or radiofrequency (RF) methods. Based on the data received at host processing unit 112, an operator can determine if the capsule and its respective blood content window are in contact with the tissue mucosa of colon 113. During the periods when the operator determines that the blood content window of the capsule endoscope 111 is not in contact with the underlying tissue mucosa, foreign matter measurements can be performed to determine if there is any foreign matter on the surface of the blood content window.

Figure 12:
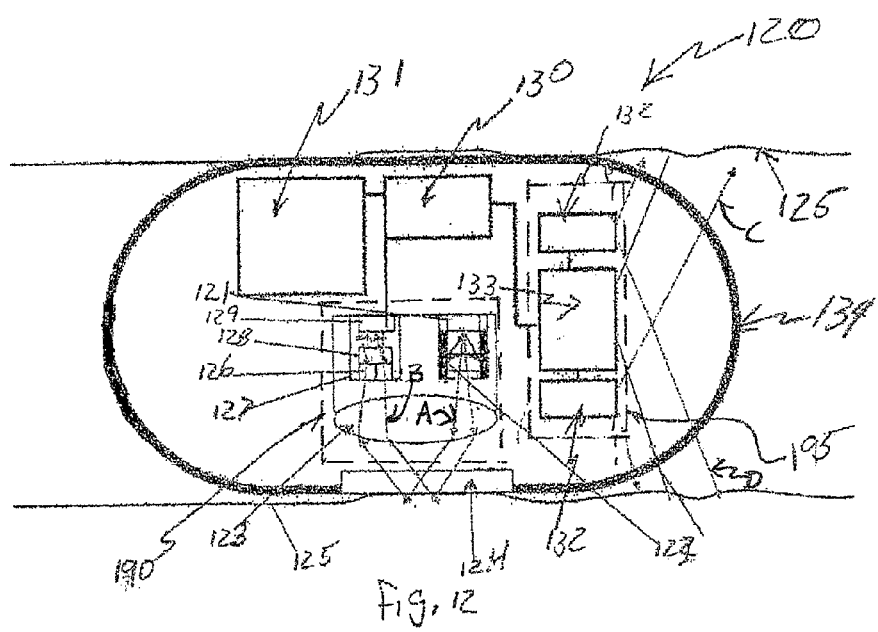
FIG. 12 depicts an exemplary embodiment of a capsule endoscope in accordance with the present invention in contact with underlying tissue.
Figure 13:
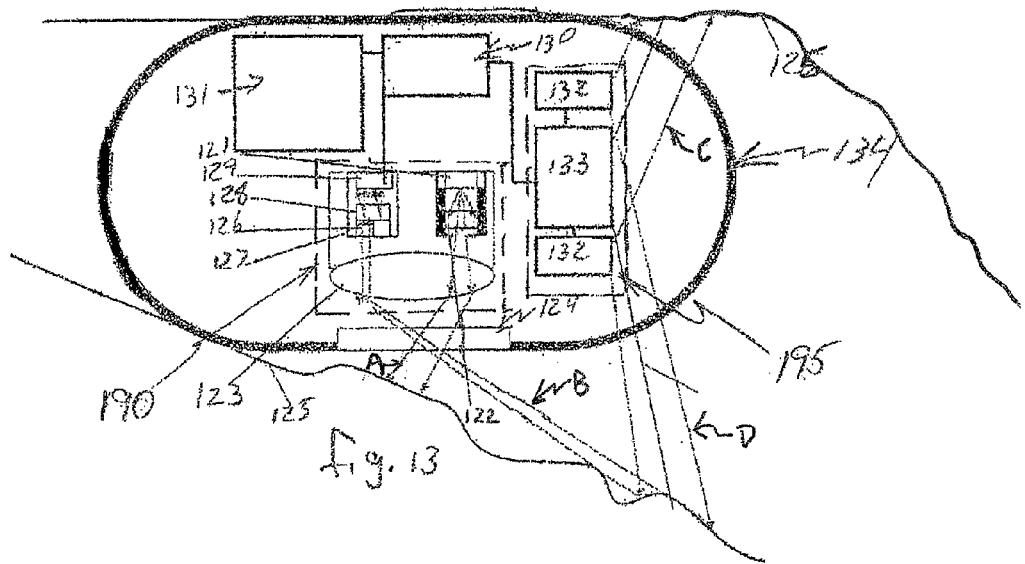
FIG. 13 depicts the exemplary embodiment of the capsule endoscope of FIG. 12 a distance from underlying tissue.

FIG. 12 depicts an exemplary capsule endoscope in contact with the tissue mucosa of the organ under investigation. FIG. 13 depicts the same endoscope capsule when the blood content sensor window 124 is not in contact with the tissue mucosa of the organ under investigation.

Capsule endoscope 120 of FIGS. 12 and 13 is comprised of four main components. Within capsule shell 134, is located (1) a power supply 130 for generating DC power to the other components of the capsule; (2) data transmitter 131 for transmitting the image data, blood content data and foreign matter data to the host processing unit; (3) a blood content sensor portion 190; and (4) a image observation portion 195. The blood content sensor portion 190 may be comprised of for example, light source 121, typically a LED or other suitable light source, a linear polarizer 122, lens 123, blood content window 124, linear polarizer 126, linear polarizer 127, transmissive grating 128 and linear sensor 129. The image observation portion 195 may include LEDs 132, and image processing unit 133, an image sensor such as a solid state sensor, e.g., CCD or other commonly used image capturing device.

Operation will now be described with respect to FIGS. 11 and 12. FIG. 12 depicts an exemplary capsule endoscope of the present invention when the blood content sensor window 124 is in contact with the tissue 125. Light source 121 receives power from power source 130 and generates light for blood content detection. The generated light (indicated by arrows A and B) passes through linear polarizer 122, lens 123, and blood content detection window 124 before striking tissue 125. The light striking living tissue 125 is scattered or reflected from and passes back through blood content sensor window 124, lens 123, and linear polarizers 126 and 127. Linear polarizers 126 and 127 are orthogonally aligned such that the light passing through linear polarizer 126 is parallel to the transmitted light and light passing through linear polarizer 127 is perpendicular to the transmitted light. The light is then spectroscopicly analyzed by transmissive grating 128 and linear sensor 129. Corresponding produced Data indicative of tissue blood content is then conveyed to data transmission unit 131 for transmission to the host unit 112.

The LEDs 132 and other components of the observation unit 190 are also powered by power supply 130 and emit light (indicated by the arrows C and D) through capsule shell 134. The emitted light illuminates the tissue 125 and an image is captured on image sensor 133. Image data is conveyed to data transmission unit 131 for transmission to the on host unit 112 of FIG. 11. Because blood content sensor window is in contact with living tissue 125, the extraneous light from LEDs 132 does not enter the blood content detection window 124 and accordingly, does not cause false or inaccurate readings.

In FIG. 13, the blood content sensor window 124 is shown not in contact with the tissue 125. Accordingly, light generated by LED 132 used for scope observation may scatter and reflect back into the blood content sensor through window 124, thereby affecting both blood content readings and foreign matter detection.

To resolve this, LEDs 132 and 121 are alternatively energized so as to not emit light simultaneously and may be characterized by the illumination timing depicted in FIG. 6. As seen in the exemplary plot of FIG. 6 broad-band light 601 in the 400 to 700 nm range is pulsed on and off. Images obtained during the on periods are transmitted back to host unit 112 for observation. During the shielding or off periods 602, LED 121 generates a light pulse 603 that is used for blood content detection and foreign matter detection. By alternating, the illumination timing for observation with the illumination timing for blood content detection the interfering light issue is eliminated. By observing the image produced on the host unit 112, an operator can determine if the capsule endoscope 120 is correctly aligned such that blood content window 124 is in contact with tissue 125.

Figure 14:
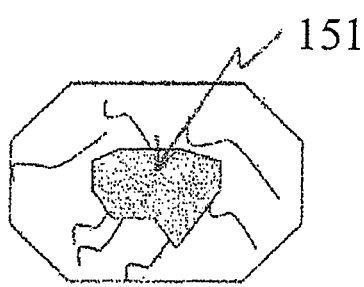
FIG. 14 depicts a representative image displayed from a capsule endoscope in accordance with the present invention in contact with underlying tissue.
Figure 15:
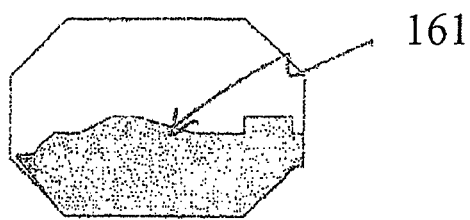
FIG. 15 depicts a representative image displayed from a capsule endoscope when the blood content sensor window is a distance from underlying tissue.

FIGS. 14 and 15 indicate exemplary images received on the host processing unit 112 when the capsule is aligned in such a way that blood content sensor window 124 is either in contact with or away from tissue 125 respectively. As seen in FIG. 14, the center of the screen 151 displays the far field of the image so that a clinician can determine that the living tissue is away from the domed surface of capsule shell 134. As can be confirmed by the image, the clinician can see by observation that the tissue is in contact with the capsule shell 134 and that the capsule is properly aligned for performing blood content measurements. Contrastingly, as depicted in FIG. 15, when capsule 120 is not aligned properly and the blood content sensor window 124 is not in contact with tissue 125, the clinician will observe that the bottom of the image 161 displayed on the screen of host processing unit 112 only displays the far field, i.e., the capsule shell 134 is separated from the tissue 125, thereby indicating to the clinician that the blood content sensor window 124 may be apart from and not in contact with the tissue 125.

If the blood content sensor window 124 is away from tissue 125, and the intensity of the blood content observation light 121 is equivalent to of greater than a set threshold of, for example, approximately 10% of the intensity typically detected for interacted light when the blood content sensor 220 is in contact with the tissue 206, it can be presumed that foreign matter is present on the window 124.

In accordance with another capsule embodiment of the invention, different light wavelength ranges are used for observation and for blood content detection in a similar manner to that described with respect to FIG. 7.

Figure 4:
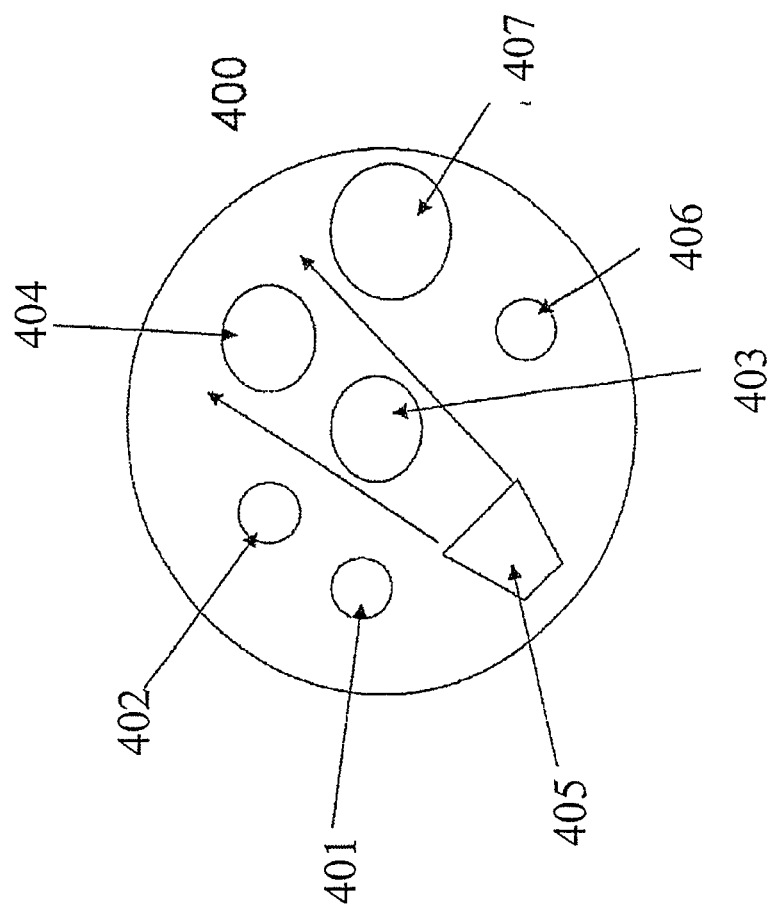
FIG. 4 illustrates an exemplary diagram of an endoscope tip usable with the present invention.

FIG. 4 depicts an exemplary embodiment of an endoscope tip for use with the present invention. Endoscope tip 400 contains a front water-supply port 401, illumination window 402, scope observation window 403, blood content sensor window 404, spray nozzle 405, illumination window 406 and utility channel 407. Scope observation window 403 and blood content sensor window 404 are linearly aligned with spray nozzle 405. When foreign matter is detected on blood content sensor window 404 by any of the methods previously described, the operator using one of any known techniques can spray water from spray nozzle 405 rinsing away foreign matter from both scope observation window 403 and blood content sensor window 404 utilizing the same spray nozzle for both, thereby minimizing the number of spray ports necessary on the endoscope tip. Further, employing this advantageous embodiment, during the rinsing of foreign matter or directly after, a foreign matter detection measurement may be performed by any of the embodiments previously disclosed to alert the operator that the blood content window is sufficiently clean and free from foreign matter to continue with blood content measurements.

Figure 16:
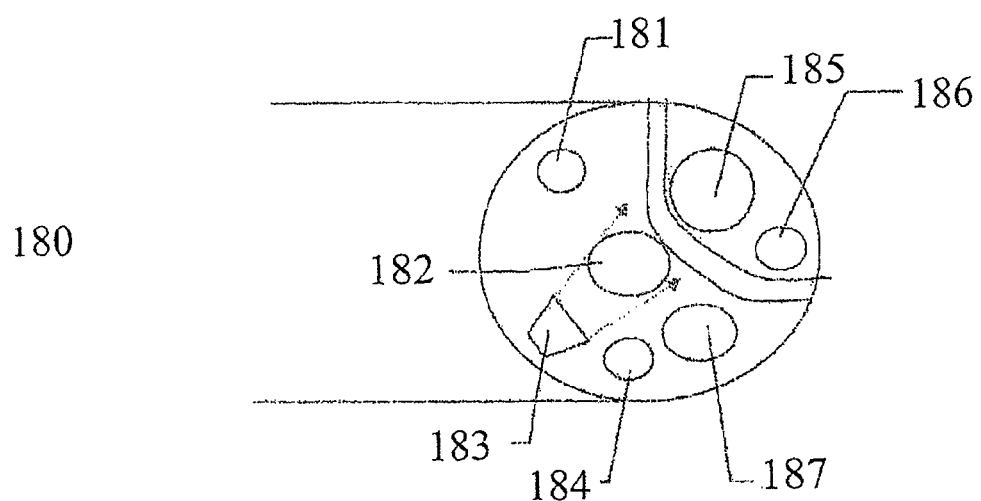
FIG. 16 illustrates an exemplary diagram of an endoscope tip usable with the present invention.
Figure 17:
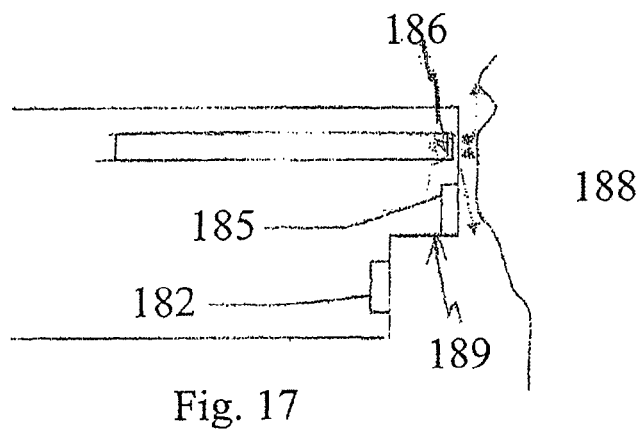
FIG. 17 illustrates a side view of the endoscope tip of FIG. 18.

Another advantageous embodiment of an endoscope tip designed to work with the present invention is described with respect to FIGS. 16 and 17. Endoscope tip 180 contains illumination window 181, scope observation window 182, spray nozzle 183, illumination window 184, blood content sensor window 185, front water supply port 186 and utility channel 187. As seen in FIG. 17, the tip of endoscope 180 resides in two planes. The forward portion 189 contains blood content window detector 185 and front water supply port 186. Because the blood content sensor widow 185 is resident on the forward portion 189, it is possible to contact the endoscope tip with tissue 188, without contacting scope observation window 182. By not contacting the scope observation window 182 with tissue 188, the image received by the operator is not saturated, and the endoscope image received via scope observation window 182 remains clear and usable. However, because the blood content sensor window 185 is on the forward portion 189, it may be difficult to rinse it with spray nozzle 183 to remove foreign matter. Instead, front water supply port 186 is used to rinse foreign matter from blood content sensor window 185. In operation, front water supply port 186 spays water onto tissue 188 and the water is reflected back onto blood content sensor window 185 rinsing away any foreign matter.

Figure 18:
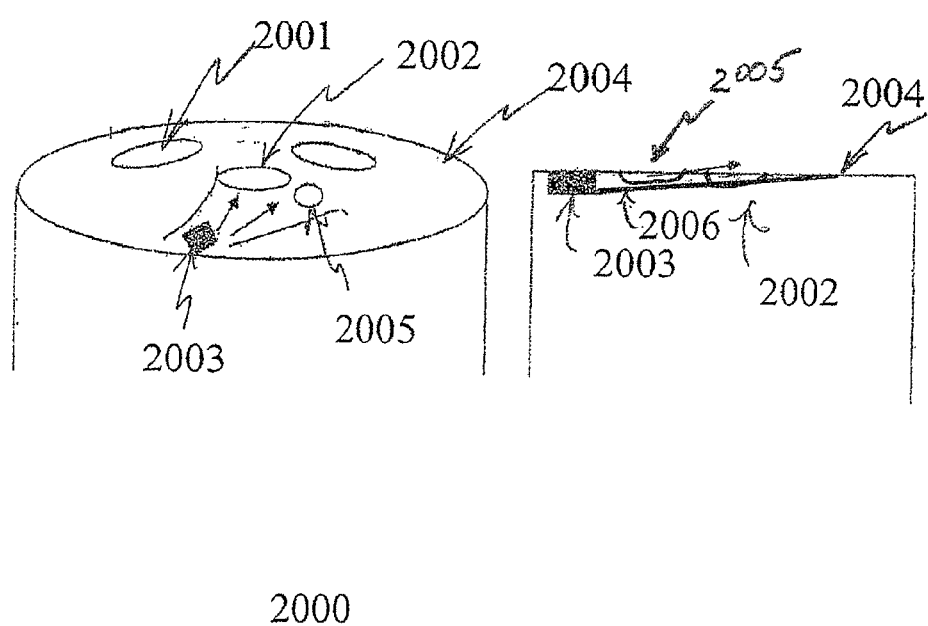
FIG. 18 illustrates an exemplary diagram of another endoscope tip configuration usable with the present invention.

FIG. 18 depicts another exemplary embodiment of an endoscope tip suitable for use with the present invention. In this embodiment, endoscope 2000 contains tip 2004, illumination window 2001, scope observation window 2002, spray nozzle 2003, and blood content sensor window 2005. Tip 2004 is generally flat, however, spray nozzle 2003 may be convex and located in a slightly inclined concave portion 2006 of tip 2004.

To improve the cleaning process of both the window for scope observation 2002 and blood content sensor window 2005, the objective lens used for scope observation 2002 and the blood content sensor window 2005 are located in an extended portion of the inclined concave portion 2006. Spray nozzle 2003, window for scope observation 2002, and blood content sensor window 2005 are arranged in the order from lower portion of the incline of 2006 to the higher portion of the slope. In this alignment, water sprayed from spray nozzle 2003 cleans both the window for scope observation 2002, and blood content sensor window 2005. The incline 2006 helps guide the water thereby improving cleaning performance, and the substantially flat tip 2004 is less likely to damage the underlying target mucosa.

While the foregoing description and drawings represent the preferred embodiments of the present invention, it will be understood that various changes and modifications may be made without departing from the spirit and scope of the present invention. For example, it is possible to combine the previously described wavelength separation and alternative timing sequencing techniques for scope observation and foreign matter detection in accordance with the invention. Although the blood content sensors used with the invention were described with respect to use with scopes, such as endoscopes or colonoscopes, it should be readily understood that the principles of the invention are equally applicable to blood content sensors employed alone or with other medical instruments.

What is claimed is:

1. A method comprising the steps of: illuminating a region of living tissue within a cavity of a body; determining if a blood content sensor is in contact with said illuminated region of tissue; detecting reflected light by said blood content sensor if it is determined that said sensor is not in contact with said illuminated tissue; wherein if the determining step determines that said blood content sensor is in contact with said illuminated region of tissue, then detecting interacted light for determining an indicator of blood content of said illuminated tissue and determining if foreign matter exist on said sensor based on said detected reflected light and validating blood content data based on a previous determination of the existence of foreign matter on said sensor.

2. The method of claim 1 further comprising the step of guiding an endoscope in said cavity based on said blood content data.

3. The method of claim 2 wherein the illuminating step further comprises the step of providing illumination of said tissue to enable visible observation of said tissue with said endoscope.

4. The method of claim 3, wherein the light used for illuminating said tissue for visible observation is within a different wavelength range then the light wavelength range used for the detecting step.

5. The method of claim 4 wherein the light used for determining blood content is a different wavelength then the light used for foreign matter detection.

6. The method of claim 4, wherein the light used for illuminating tissue for visible observation is sequential emission of red, green and blue light.

7. The method of claim 4, wherein the light used for illuminating tissue for visible observation is broadband light.

8. The method of claim 3 wherein the light used for illuminating said tissue and for determining blood content are alternatively emitted.

9. A method for determining foreign matter on a blood content sensor comprising the steps of:
   illuminating mucosal tissue within a cavity of a body with polarized light in one wavelength range;
   determining if a blood content sensor is in contact with said illuminated mucosal tissue;
   detecting interacted light within a first wavelength range by said blood content sensor-to measure blood content within said illuminated tissue if it is determined that the blood content sensor is in contact with said illuminated mucosal tissue;
   detecting reflected light within a second wavelength range by said blood content sensor if it is determined that the blood content sensor is not in direct contact to measure blood content; and determining if foreign matter exist on said blood content sensor based on said detected light from the second wavelength range.

10. An apparatus for determining foreign matter on a blood content sensor comprising:
   an illuminator configured to illuminate mucosal tissue within a body cavity;
   a blood content sensor configured to detect reflected and/or interacted light from the mucosal tissue and generate a corresponding signal;
   a contact sensor configured to detect if the blood content sensor is in contact with said illuminated region of tissue; and
   a processor coupled to the blood content sensor and the contact sensor, said processor configured to analyze the signal, and determine blood content within said mucosal tissue based upon said signal when said contact detector detects that said blood content sensor is in contact with said mucosal tissue, and wherein said processor is further configured to detect the presence of foreign matter on said blood content sensor based upon said signal when said contact detector detects that said sensor is not in contact with said mucosal tissue.

11. An apparatus for detecting blood content within mucosal tissue comprising:
   a first illuminator configured to illuminate mucosal tissue within a body cavity with light within a first wavelength range;
   a first sensor configured to detect blood content in the mucosal tissue, the first sensor including a window and a receiver configured to receive interacted light from the mucosal tissue through the window and generate a corresponding data signal;
   a second illuminator configured to illuminate the mucosal tissue with light within a second wavelength range different from the first wavelength range;
   a second sensor configured to visibly observe the mucosal tissue based on light from the second illuminator reflected by the mucosal tissue;
   a contact sensor arranged near the first illuminator and configured to detect whether or not the first sensor is in contact with the mucosal tissue, and
   a processor coupled to the first sensor and the contact sensor, said processor configured to analyze the data signal and to generate an output signal indicating presence of foreign matter on the window; said processor further configured to (a) determine whether or not the output signal indicating presence of an foreign matter on the window is generated in accordance with the received reflected light when the contact sensor detects that the first sensor is not in contact with the mucosal tissue, and (b) determine blood content within the mucosal tissue in accordance with the received interacted light when the contact sensor detects that the first sensor is in contact with the mucosal tissue.

12. A method for detecting blood content within mucosal tissue comprising the steps of:
   illuminating mucosal tissue within a body cavity with light in a first wavelength range;
   determining if a blood content sensor is in contact with said illuminated mucosal tissue;
   detecting interacted light in the first wavelength range from the illuminated mucosal tissue using a blood content sensor and calculating blood content within said illuminated tissue if it is determined that the blood content sensor is in contact with said illuminated mucosal tissue;
   illuminating the mucosal tissue with light in a second wavelength range different from the first wavelength range;
   detecting reflected light in the second wavelength range from the illuminated mucosal tissue if it is determined that the blood content sensor is not in contact with said illuminated mucosal tissue; and
   determining if foreign matter exist on said blood content sensor based on said detected reflected light in the second wavelength range.

\* \* \* \* \*